United States Patent
Dickens (10) Patent No.: US 10,159,284 B2
(45) Date of Patent: Dec. 25, 2018

(54) AEROSOL PROVISION SYSTEM WITH AN AIR CHANNEL WALL WITH A SURFACE FINISH TO INCREASE WETTABILITY, AND RELATED METHOD

(71) Applicant: Nicoventures Holdings Limited, London (GB)

(72) Inventor: Colin John Dickens, London (GB)

(73) Assignee: Nicoventures Holdings Limited, London (GB)

( * ) Notice: Subject to any disclaimer, the term of this patent is extended or adjusted under 35 U.S.C. 154(b) by 0 days.

(21) Appl. No.: 15/316,435

(22) PCT Filed: Jun. 11, 2015

(86) PCT No.: PCT/GB2015/051722
§ 371 (c)(1),
(2) Date: Dec. 5, 2016

(87) PCT Pub. No.: WO2015/189623
PCT Pub. Date: Dec. 17, 2015

(65) Prior Publication Data
US 2017/0143038 A1 May 25, 2017

(30) Foreign Application Priority Data

Jun. 13, 2014 (GB) .................. 1410562.1

(51) Int. Cl.
*A24F 47/00* (2006.01)
*A61M 15/06* (2006.01)

(52) U.S. Cl.
CPC ........... *A24F 47/008* (2013.01); *A61M 15/06* (2013.01)

(58) Field of Classification Search
None
See application file for complete search history.

(56) References Cited

U.S. PATENT DOCUMENTS

| 4,765,347 A | * | 8/1988 | Sensabaugh, Jr. .... A24F 47/002 131/173 |
| 5,505,214 A | | 4/1996 | Collins et al. |

(Continued)

FOREIGN PATENT DOCUMENTS

| CN | 202941411 U | 5/2013 |
| CN | 203353688 U | 12/2013 |

(Continued)

OTHER PUBLICATIONS

International Search Report for corresponding International Application No. PCT/GB2015/051722 dated Aug. 4, 2015; 6 pages.

(Continued)

*Primary Examiner* — Tho D Ta
(74) *Attorney, Agent, or Firm* — Patterson Thuente Pedersen, P.A.

(57) ABSTRACT

An aerosol provision system, such as an electronic cigarette, comprises an aerosol source for generating an aerosol from a source liquid comprising a liquid formulation, for example containing nicotine, is described. The system comprises an air channel arranged between the aerosol source and a mouthpiece opening through which a user inhales the aerosol during use. The air channel is defined by a wall, and at least a portion of an inner surface of the wall is provided with a surface finish to increase the wettability of the surface to the liquid formulation. Increasing the wettability of the air channel can help reduce the likelihood of the aerosol condensing into droplets of the liquid formulation on the walls of the air channel and being drawn into a user's mouth therefrom.

20 Claims, 3 Drawing Sheets

(56) References Cited

U.S. PATENT DOCUMENTS

| | | |
|---|---|---|
| 5,666,977 A | 9/1997 | Higgins et al. |
| 6,390,453 B1 | 5/2002 | Frederickson et al. |
| 8,833,364 B2 | 9/2014 | Buchberger |
| 9,555,199 B2 * | 1/2017 | Buchberger .......... A61M 11/041 |
| 2003/0062042 A1 | 4/2003 | Wensley et al. |
| 2011/0011398 A1 | 1/2011 | Yeates |
| 2011/0011899 A1 | 1/2011 | Yeates |
| 2011/0226236 A1 | 9/2011 | Buchberger |
| 2011/0266563 A1 * | 11/2011 | Peter .................. B82Y 10/00 257/88 |
| 2012/0104637 A1 | 5/2012 | Daehnert |
| 2013/0019647 A1 | 1/2013 | Inoue |
| 2014/0109905 A1 | 4/2014 | Yamada |
| 2017/0042221 A1 | 2/2017 | England |

FOREIGN PATENT DOCUMENTS

| | | |
|---|---|---|
| EP | 0244684 | 11/1987 |
| EP | 1005917 A1 | 6/2000 |
| EP | 2070682 A1 | 6/2009 |
| EP | 2 708 219 A1 | 3/2014 |
| WO | WO2012109371 | 8/2012 |
| WO | WO 2013/124357 A1 | 8/2013 |

OTHER PUBLICATIONS

Written Opinion of the International Searching Authority for corresponding International Application No. PCT/GB2015/051722 dated Aug. 4, 2015; 6 pages.

Notification of International Preliminary Report on Patentability, International Application No. PCT/GB2015/051722, dated Dec. 15, 2016, 8 pages.

Canadian Office Action, Application No. 2,949,434, dated Jul. 3, 2018, 5 pages.

Australian Examination Report, Application No. 2015273220, dated May 18, 2018, 5 pages.

Chinese Office Action, Application No. 201580031469.4, dated Jul. 25, 2018, 8 pages (18 pages with translation).

* cited by examiner

AEROSOL PROVISION SYSTEM WITH AN AIR CHANNEL WALL WITH A SURFACE FINISH TO INCREASE WETTABILITY, AND RELATED METHOD

CROSS-REFERENCE TO RELATED APPLICATIONS

The present application is a National Phase entry of PCT Application No. PCT/GB2015/051722, filed on 11 Jun. 2015, which claims priority to GB Patent Application No. 1410562.1, filed on 13 Jun. 2014, which are hereby fully incorporated herein by reference.

TECHNICAL FIELD

The present disclosure relates to aerosol provision systems such as nicotine delivery systems (e.g. e-cigarettes).

BACKGROUND

Aerosol provision systems such as e-cigarettes generally contain a reservoir of a source liquid containing a formulation, typically including nicotine, for which an aerosol is generated, e.g. through vaporization or other means. Thus an aerosol source for an aerosol provision system may comprise a heater coupled to a portion of the source liquid from the reservoir. When a user inhales on the device, the heater is activated to vaporize a small amount of the source liquid, which is thus converted to an aerosol for inhalation by the user. More particularly, such devices are usually provided with one or more air inlet holes located away from a mouthpiece of the system. When a user sucks on the mouthpiece, air is drawn in through the inlet holes and past the aerosol source. There is a flow path connecting between the aerosol source and an opening in the mouthpiece so that air drawn past the aerosol source continues along the flow path to the mouthpiece opening, carrying some of the aerosol from the aerosol source with it. The aerosol-carrying air exits the aerosol provision system through the mouthpiece opening for inhalation by the user.

A problem can arise in aerosol provision systems of the kind discussed above whereby a portion of the aerosol may deposit (condense) on an inner wall of the flow path connecting the aerosol source to the mouthpiece opening. This can lead to the build-up of droplets of the formulation from the source liquid forming on the wall of the flow path. These droplets may then become entrained in air flowing through the flow path and drawn into a user's mouth. This can detract from the user's experience, for example, because the droplets may be tasted. This problem may in some respects be referred to as mouth leakage.

Some issues relating to aerosol condensation in an inhaler have been previously considered in US 2011/0226236. In particular, US 2011/0226236 recognizes a desire to avoid frequent changes of mouthpiece resulting from condensate build-up. To address this issue, US 2011/0226236 proposes using an absorbent body in conjunction with a cooler to capture and store components of the aerosol that might otherwise condense in the mouthpiece. The approach of US 2011/0226236 has drawbacks in that it relies on a relatively complex two-stage solution that takes up space in the inhaler.

Accordingly there remains a need for aerosol provision systems which seek to ameliorate some of the issues discussed above relating to aerosol condensation.

SUMMARY

According to an aspect of certain embodiments, there is provided an aerosol provision system comprising an aerosol source for generating an aerosol from a source liquid comprising a liquid formulation; and an air channel wall defining an air channel connecting between the aerosol source and an opening through which a user can inhale the aerosol during use; and wherein at least a portion of an inner surface of the air channel wall is provided with a surface finish to increase its wettability for the liquid formulation.

According to an aspect of certain embodiments, there is provided a method of manufacturing an aerosol provision system comprising an aerosol source for generating an aerosol from a source liquid comprising a liquid formulation and an air channel wall defining an air channel connecting between the aerosol source and an opening through which a user can inhale the aerosol during use, wherein the method comprises applying a surface finish to at least a portion the air channel wall to increase its wettability for the liquid formulation.

According to an aspect of certain embodiments, there is provided an apparatus for manufacturing an air channel wall for an aerosol provision system comprising an aerosol source for generating an aerosol from a source liquid comprising a liquid formulation and the air channel wall defining an air channel connecting between the aerosol source and an opening through which a user can inhale the aerosol during use, wherein the apparatus comprises a mechanism for applying a surface finish to at least a portion the air channel wall to increase its wettability for the liquid formulation.

The approach described herein is not restricted to specific embodiments such as set out below, but includes and contemplates any appropriate combinations of features presented herein. For example, an electronic aerosol provision system may be provided in accordance with the approach described herein which includes any one or more of the various features described below as appropriate.

BRIEF DESCRIPTION OF THE DRAWINGS

Various embodiments will now be described in detail by way of example only with reference to the following drawings:

FIG. 1 is a schematic (exploded) diagram of an aerosol provision system such as an e-cigarette in accordance with some embodiments.

FIG. 2 is a schematic diagram of a main body portion of the e-cigarette of FIG. 1 in accordance with some embodiments.

FIG. 3 is a schematic diagram of an aerosol source portion of the e-cigarette of FIG. 1 in accordance with some embodiments.

FIG. 4 is a schematic diagram showing certain aspects of one end of the main body portion of the e-cigarette of FIG. 1 in accordance with some embodiments.

FIGS. 5A to 5C are schematic diagrams of components of an aerosol provision system in accordance with some other embodiments.

FIG. 6 is a flow diagram schematically representing steps in a method of manufacturing an aerosol provision system in accordance with some embodiments.

FIG. 7 is a schematic diagram of an apparatus for manufacturing an aerosol provision system in accordance with some embodiments.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to an aerosol provision system, such as an e-cigarette. Throughout the following description the term "e-cigarette" is sometimes used; however, this term may be used interchangeably with aerosol (vapor) provision system.

Figure 1:
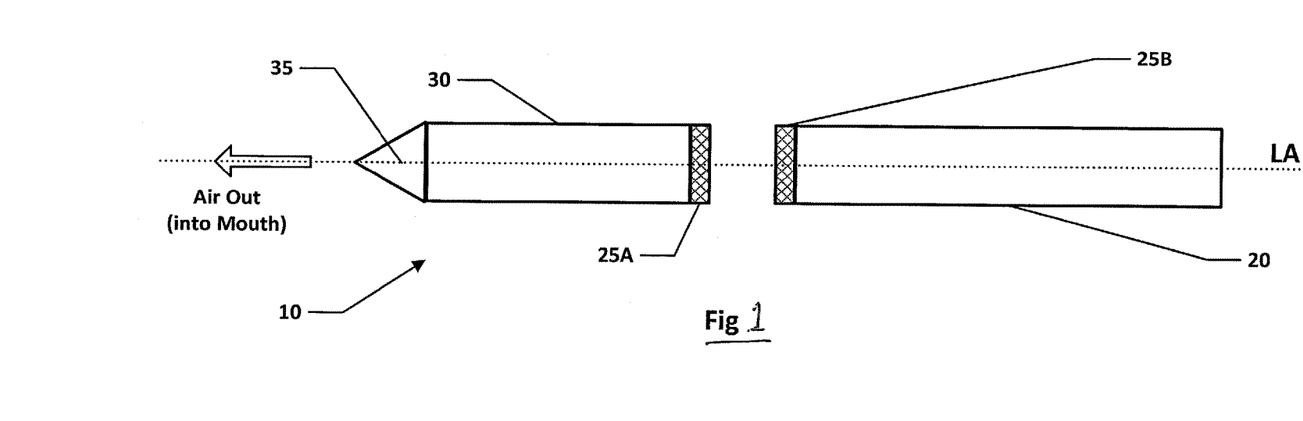

FIG. 1 is a schematic diagram of an aerosol/vapor provision system such as an e-cigarette 10 in accordance with some embodiments (not to scale). The e-cigarette has a generally cylindrical shape, extending along a longitudinal axis indicated by dashed line LA, and comprises two main components, namely a body 20 and a cartomizer 30. The cartomizer includes an internal chamber containing a reservoir of a source liquid comprising a liquid formulation from which an aerosol is to be generated, for example containing nicotine, and an aerosol generator. The source liquid and the aerosol generator may be collectively referred to as an aerosol source. The cartomizer 30 further includes a mouthpiece 35 having an opening through which a user may inhale the aerosol generated by the aerosol source. The source liquid may be of a conventional kind used in the cigarettes, for example comprising around 3% nicotine and 50% glycerol, with the remainder comprising roughly equal measures of water and propylene glycol, and possibly other components, such as flavorings. The reservoir for the source liquid may comprise a foam matrix or any other structure within a housing for retaining the liquid source liquid until such time that it is required to be delivered to the aerosol generator/vaporizer. The aerosol generator includes a heater for vaporizing the source liquid to form the aerosol of the liquid formulation. The aerosol generator may further include a wick or similar facility to transport a small amount of the source liquid from the reservoir to a heating location on or adjacent the heater.

The body 20 includes a re-chargeable cell or battery to provide power for the e-cigarette 10 and a circuit board for generally controlling the e-cigarette. In use, when the heater receives power from the battery, as controlled by the circuit board, the heater vaporizes source liquid at the heating location to generate the aerosol, and this is then inhaled by a user through the opening in the mouthpiece. The aerosol is carried from the aerosol source to the mouthpiece along an air channel that connects the aerosol source to the mouthpiece opening as a user inhales on the mouthpiece.

In this particular example, the body 20 and cartomizer 30 are detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector on the body 20 that is used to connect to the cartomizer also serves as a socket for connecting a charging device (not shown) when the body is detached from the cartomizer 30. The other end of the charging device can be plugged into an external power supply, for example a USB socket, to charge or to re-charge the cell/battery in the body of the e-cigarette. In other implementations, a cable may be provided for direct connection between the electrical connector on the body and the external power supply.

The e-cigarette 10 is provided with one or more holes (not shown in FIG. 1) for air inlet. These holes connect to an air running passage through the e-cigarette 10 to the mouthpiece 35. The air passage includes a region around the aerosol source and a section comprising an air channel connecting from the aerosol source to the opening in the mouthpiece.

When a user inhales through the mouthpiece 35, air is drawn into this air passage through the one or more air inlet holes, which are suitably located on the outside of the e-cigarette. This airflow (or the resulting change in pressure) is detected by a pressure sensor that in turn activates the heater to vaporize a portion of the liquid source to generate the aerosol. The airflow passes through the air passage, and combines with, the aerosol in the region around the aerosol source, and the resulting combination of airflow and aerosol then travel along the air channel connecting from the aerosol source to the mouthpiece 35 to be inhaled by a user. The cartomizer 30 may be detached from the body 20 and disposed of when the supply of source liquid is exhausted (and replaced with another cartomizer if so desired). Alternatively, the customers are maybe refillable.

It will be appreciated the e-cigarette 10 shown in FIG. 1 is presented by way of example, and various other implementations can be adopted. For example, in some embodiments, the cartomizer 30 is provided as two separable components, namely a cartridge comprising the source liquid reservoir and mouthpiece (which can be replaced when the source liquid from the reservoir is exhausted), and a vaporizer/aerosol generator comprising a heater (which is generally retained). As another example, the charging facility may connect to an additional or alternative power source, such as a car cigarette lighter socket.

Figure 2:
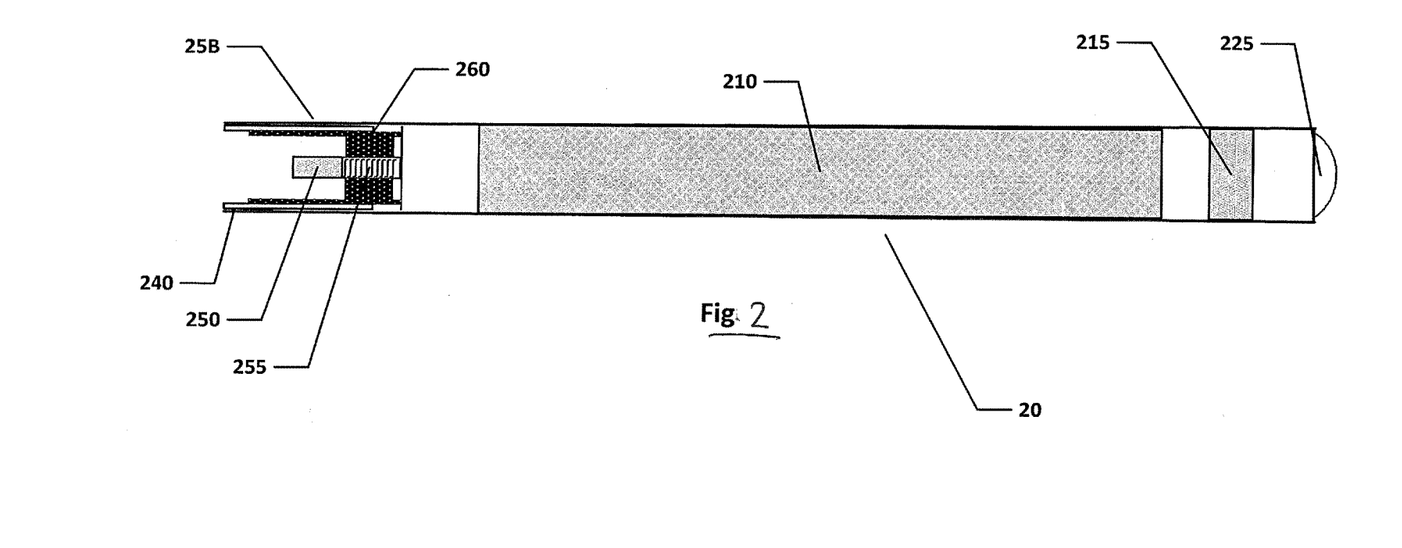

FIG. 2 is a schematic (simplified) diagram of the body 20 of the e-cigarette of FIG. 1. FIG. 2 can generally be regarded as a cross-section in a plane through the longitudinal axis LA of the e-cigarette. Note that various components and details of the body, e.g. such as wiring and more complex shaping, have been omitted from FIG. 2 for reasons of clarity.

As shown in FIG. 2, the body 20 includes a battery or cell 210 for powering the e-cigarette 10, as well as a chip, such as an application specific integrated circuit (ASIC) or microcontroller for controlling the e-cigarette 10. The ASIC may be positioned alongside or at one end of the battery 210. The ASIC is attached to a sensor unit 215 to detect an inhalation on mouthpiece 35 (or alternatively the sensor unit 215 may be provided on the ASIC itself). In response to such a detection, the ASIC provides power from the battery or cell 210 to the heater in the cartomizer to vaporize source liquid and introduce an aerosol into the airflow which is inhaled by a user.

The body further includes a cap 225 to seal and protect the far (distal) end of the e-cigarette. There is an air inlet hole provided in or adjacent to the cap 225 to allow air to enter the body and flow past the sensor unit 215 when a user inhales on the mouthpiece 35. This airflow therefore allows the sensor unit 215 to detect the user inhalation and so activate the aerosol generator element of the e-cigarette.

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer pushes against the electrical contact 250 in such a manner as to compress the coil spring in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A, thereby helping to ensure good electrical connectivity between the body 20 and the cartomizer 30. The body connector 240 and the electrical contact 250 are separated by a trestle 260, which is made of a non-conductor (such as plastic) to provide good insulation between the two electrical terminals. The trestle 260 is shaped to assist with the mutual mechanical engagement of connectors 25A and 25B.

Figure 3:
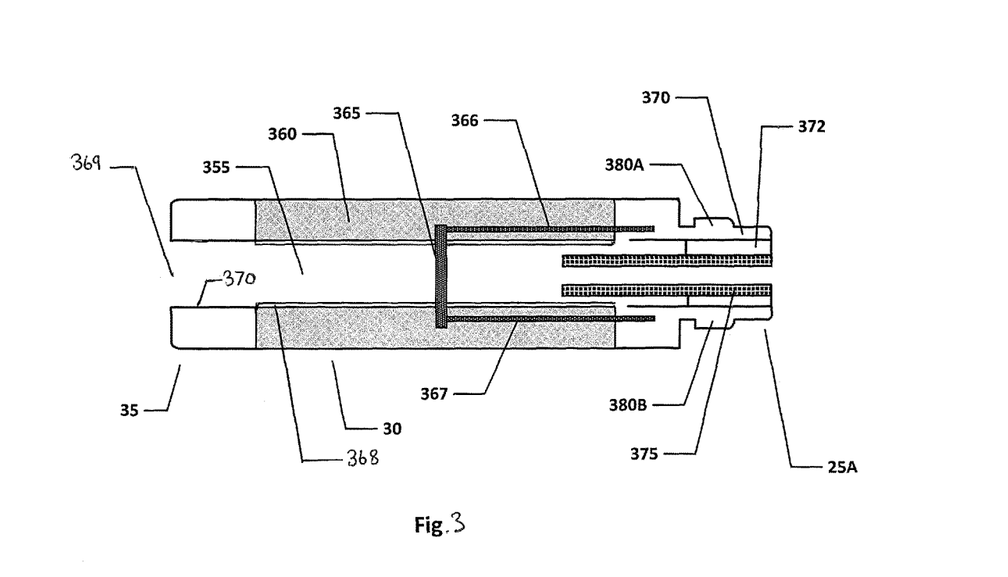

FIG. 3 is a schematic diagram of the cartomizer 30 of the e-cigarette of FIG. 1 in accordance with some embodiments. FIG. 3 can generally be regarded as a cross-section in a plane through the longitudinal axis LA of the e-cigarette. Note that various components and details of the body, e.g. such as wiring and more complex shaping, have been omitted from FIG. 3 for reasons of clarity.

The cartomizer 30 includes an air passage 355 extending along the central (longitudinal) axis of the cartomizer 30 from the mouthpiece 35 to the connector 25A for joining the cartomizer to the body 20.

A reservoir of source liquid 360 is provided around the air passage 335. This reservoir 360 may be implemented, for example, by providing cotton or foam soaked in source liquid. The cartomizer also includes a heater 365 for heating source liquid from the reservoir 360 to generate an aerosol to flow through air passage 355 and out through an opening 369 in the mouthpiece 35 in response to a user inhaling on the e-cigarette 10. The heater is powered through lines 366 and 367, which are in turn connected to opposing polarities (positive and negative, or vice versa) of the battery 210 via connector 25A (the details of the wiring between the power lines 366 and 367 and connector 25A are omitted from FIG. 3).

A section of the air passage 355 between the heater 365 and the mouthpiece opening 369 provides an air channel along which the aerosol-laden air passes during use of the e-cigarette. This air channel is defined by an air channel wall, which in this example comprises a first portion 368 and a second portion 370. The first portion 368 of the air channel wall comprises an inner wall of the source liquid reservoir 360 surrounding the air channel and the second portion 370 comprises an inner surface of the mouthpiece 35 surrounding the air channel. As discussed further below, one significant aspect of the e-cigarette in accordance with certain embodiments is that at least a portion of the surface of the inner wall 368; 370 defining the air channel connecting between the aerosol source 360; 365 and the mouthpiece opening is provided with a surface finish to increase its wettability for the liquid formulation from which the aerosol is generated.

The connector 25A includes an inner electrode 375, which may be silver-plated or made of some other suitable metal. When the cartomizer 30 is connected to the body 20, the inner electrode 375 contacts the electrical contact 250 of the body 20 to provide a first electrical path between the cartomizer and the body. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring is surrounded by the cartomizer connector 370, which may be silver-plated or made of some other suitable metal or conducting material. When the cartomizer 30 is connected to the body 20, the cartomizer connector 370 contacts the body connector 240 of the body 20 to provide a second electrical path between the cartomizer and the body. In other words, the inner electrode 375 and the cartomizer connector 370 serve as positive and negative terminals (or vice versa) for supplying power from the battery 210 in the body to the heater 365 in the cartomizer via supply lines 366 and 367 as appropriate.

The cartomizer connector 370 is provided with two lugs or tabs 380A, 380B, which extend in opposite directions away from the longitudinal axis of the e-cigarette. These tabs are used to provide a bayonet fitting in conjunction with the body connector 240 for connecting the cartomizer 30 to the body 20. This bayonet fitting provides a secure and robust connection between the cartomizer 30 and the body 20, so that the cartomizer 30 and body 20 are held in a fixed position relative to one another, without wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
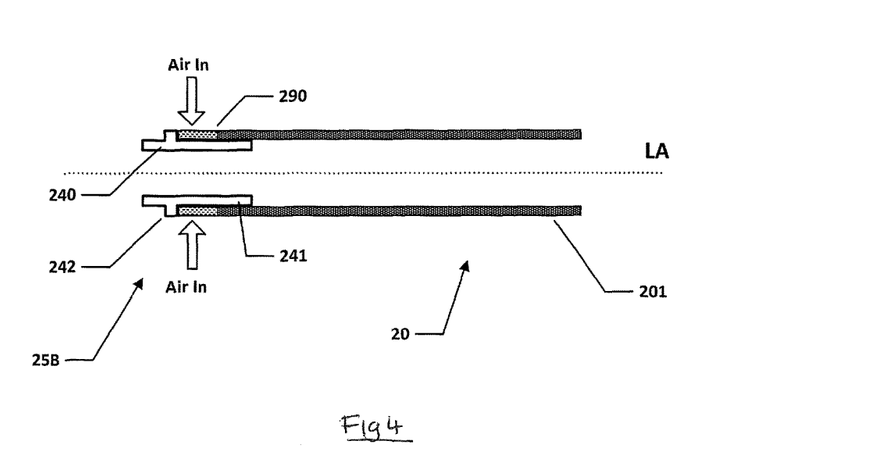

FIG. 4 is a schematic diagram of certain details of the connector 25B at the end of the body 20 in accordance with some embodiments (but omitting for clarity most of the internal structure of the connector as shown in FIG. 2, such as trestle 260). In particular, FIG. 4 shows the external housing 201 of the body 20, which generally has the form of a cylindrical tube. This external housing 201 may comprise, for example, an inner tube of metal with an outer covering of paper or similar.

The body connector 240 extends from this external housing 201 of the body 20. The body connector as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette. Surrounding the shaft portion 241 of the body connector 240, where the shaft portion does not overlap with the external housing 201, is a collar or sleeve 290, which is again in a shape of a cylindrical tube. The collar 290 is retained between the lip portion 242 of the body connector 240 and the external housing 201 of the body, which together prevent movement of the collar 290 in an axial direction (i.e. parallel to axis LA). However, collar 290 is free to rotate around the shaft portion 241 (and hence also axis LA).

As mentioned above, the cap 225 is provided with an air inlet hole to allow air to flow past sensor 215 when a user inhales on the mouthpiece 35. However, the majority of air that enters the device when a user inhales flows through collar 290 and body connector 240 as indicated by the two arrows in FIG. 4.

As discussed above, a portion of the aerosol passing down the air channel 355 may condense onto the inner surface of the wall 368, 370 defining the air channel during use of the e-cigarette. In a conventional e-cigarette this condensation of aerosol may aggregate on the air chamber wall to form droplets which the inventor has recognized may become entrained in the airflow passing through the air channel and out the mouthpiece opening 369 into a user's mouth, thereby detracting from the user's experience.

To seek to ameliorate this issue, at least a portion of the surface of the inner wall 368; 370 defining the air channel connecting between the aerosol source 360; 365 and the mouthpiece opening 369 is provided with a surface finish to increase its wettability for the liquid formulation from which the aerosol is generated. Thus in accordance with certain example embodiments, an aerosol provision system (e-cigarette) may be conventional apart from the provision of a surface finish applied to the wall(s) of an air channel connecting from the source of the aerosol to the mouthpiece to increase the wettability of these walls to the liquid formulation comprising the aerosol.

By increasing the wettability of the walls of the air channel, the liquid formulation condensing out of the aerosol onto the walls of the air channel is encouraged to spread to form a film (i.e. adopt a relatively low contact angle) rather than bead into droplets (i.e. adopt a relatively high contact angle). This can help to lower the likelihood of the liquid formulation deposited on the air channel wall from being entrained in (i.e. picked up by) air drawn through the air channel as a user inhales on the aerosol provision system during normal use. That is to say, the increased wettability of the walls reduces the contact angle of liquid formulation condensing onto the walls of the air channel from the aerosol, thereby making the liquid formulation less likely to detach from the wall and enter the air flow in the air channel than would otherwise be the case (i.e. without a surface treatment to increase wettability of at least a portion of the interior surface defining the air channel).

There are a number of different surface finishes that may be applied to (at least a portion of) the inner wall of the air channel to increase its wettability with respect to the liquid formulation. For example, the surface finish may comprise a plasma-coating treatment provided in accordance with conventional techniques to increase wettability. In another example, the air channel wall may comprise a substrate which is structurally well suited to forming the air channel, for example in terms of manufacturing cost and simplicity, but which has relatively low wettability (high contact angle/low adhesion) for the liquid formulation. The surface finish to increase wettability may thus comprise a coating applied to the substrate, wherein the coating has a higher wettability (lower contact angle/higher adhesion) for the liquid formulation than the substrate. For example, the coating may comprise a material having a relatively high solid surface free energy surface as compared to the substrate.

However, in the example of the e-cigarette represented in FIGS. 1 to 4, the surface finish provided to increase the wettability of at least a portion of the inner surface of the air channel connecting between the source of the aerosol and the mouthpiece comprises surface texturing. The nature of the surface texturing, for example in terms of the physical scale of the texture pattern, may be selected to provide the increased wettability characteristics in accordance with the established principles regarding how surface texturing affects wettability. The surface texturing may be provided in a number of different ways. For example, in some implementations, the surface texture may be applied by abrasive roughening of the relevant surface of the air channel wall, for example by rubbing with an abrasive element. However, an approach which is likely to be simpler for large scale manufacturing is for the surface texture to be molded into relevant parts of the aerosol provision system (i.e. the parts defining the air channel wall) during manufacturing. The relevant parts of the aerosol provision system providing the air channel wall will typically be manufactured through a plastic molding process, and therefore surface texture can be readily applied by using a mould having a suitably textured surface. An advantage of this approach is that it requires relatively very little change to existing manufacturing apparatus and methods for the relevant components of aerosol provision systems. Furthermore, once the change has been made (i.e. once the relevant parts of the molding apparatus are provided with the desired surface texturing), the number of manufacturing steps associated with each individual aerosol provision system, and the manner in which the components of the aerosol provision systems are handled during manufacture, remains the same as for conventional aerosol provision systems.

The characteristics of a particular surface texture, for example in terms of a characteristic spatial scale for the structures comprising the texturing, may in some cases be determined empirically. For example, the wettability of different samples of the material comprising the relevant part of the air channel wall may be measured for the liquid formulation for a range of different surface texture characteristics. An appropriate surface texture characteristic may then be selected from among the test samples having regard to their observed wettability characteristics for the liquid formulation. By way of a specific example, in some embodiments a surface roughness of around, or at least, a surface roughness corresponding to N10, N11 or N12 (according to the ISO1312 definition) might be used. However, other degrees of surface roughness/texture, for example around, or at least, N1, N2 or N3 could be used in other embodiments.

A similar empirical approach for establishing appropriate surface finish characteristics can similarly be adopted when using other techniques to increase the wettability of the surface, for example for implementations using a surface coating finish.

An approach of applying a surface finish to modify wettability for an air channel of an aerosol provision system to seek to reduce mouth leakage has been described above in the context of a relatively schematic e-cigarette. It will, however, be appreciated these principles can be applied for various different types of aerosol provision system/e-cigarette regardless of the underlying technology (for example in terms of the aerosol generation technique) and other design aspects (for example in terms of overall size and shape) underlying the aerosol provision system.

Figures 5A, 5B:
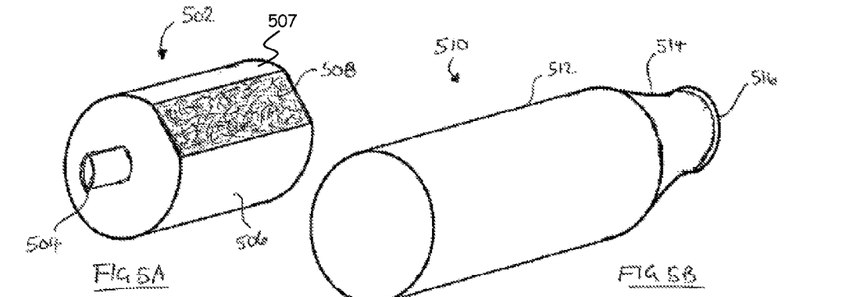
Figure 5C:
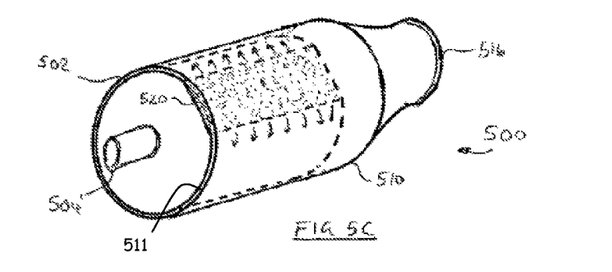

FIGS. 5A to 5C schematically represent in perspective view some aspects of part an aerosol provision system 500 according to some other embodiments. In particular, FIG. 5A schematically represents a first component comprising an aerosol source 502 and FIG. 5B schematically represents a second component 510 comprising part of a housing for the aerosol provision system 500. These two components of the aerosol provision system 500 are shown separately in FIGS. 5A and 5B for ease of representation, whereas in normal use these two components are assembled together as schematically represented in FIG. 5C. In the assembled state for this particular design of aerosol provision system, the aerosol source component 502 is fitted inside the housing component 510. It will be appreciated the aerosol provision system 500 will in general comprise various other features, for example a power supply, which are not shown in FIGS. 5A to 5C for simplicity. Such other features of the aerosol provision system may be provided in accordance with conventional techniques. More generally, it will be appreciated that aspects and features of aerosol provision systems described herein may be implemented in accordance with any established techniques apart from where modified in accordance with the embodiments described herein.

The aerosol source component 502 comprises a reservoir body 506 containing a source liquid comprising liquid formulation from which an aerosol is to be generated and an aerosol generator 504, for example based on a heater. The source liquid and the aerosol generator 504 may by conventional. The reservoir body 506 is generally in the form of a circular cylinder with a flat face 508 running longitudinally along one side. The reservoir body 506 may be formed in accordance with conventional techniques, for example comprising a molded plastics material.

The housing component 510 is generally tubular and circularly symmetric. The housing component 510 comprises a main housing component 512 and a mouthpiece component 514. These may be formed separately or integrally. The main housing component 512 and mouthpiece component 514 may be formed in accordance with conventional techniques, for example comprising extruded aluminum or molded plastic. The main housing component 512 comprises a generally cylindrical tube having an interior dimension conforming to the exterior dimension of the aerosol source component 502. Thus the aerosol source component 502 can be received within the housing component 510 in a close-fitting arrangement, as schematically represented in FIG. 5C. It will be appreciated the housing component 510 will in general extend further than represented in FIG. 5C so as to generally enclose the aerosol generator 504. The mouthpiece component 514 of the housing component 510 is contoured to provide a transition from the shape of the main housing component to a shape which is ergonomically suited to be received by a user's lips during use. The mouthpiece component 514 includes an opening 516 at the end through which a user may inhale aerosol generated by the aerosol source.

As can be seen from the schematic representation in FIG. 5C, when the aerosol source component 502 is inserted into the housing component 510, the provision of the flat surface 508 creates a spacing between the outside wall of the reservoir body 506 and the inside wall of the housing component 510. This region where the first component 502 and the second component 510 of the aerosol provision system 500 are spaced apart thereby defines part of an air channel 520 connecting from the vicinity of the aerosol generator 504 to the opening 516. Other parts of the air channel are defined by the interior of the housing 510 that does not surround the aerosol source component 502 adjacent to the mouthpiece 514 and the interior surface of the mouthpiece 514. In general there may be further structural elements of the aerosol provision system in these regions to define the air channel 520. For example, flow restrictors and/or baffles and/or switchbacks may be provided to govern the airflow in accordance with conventional techniques.

The general operating principles of the aerosol provision system 500 schematically represented in FIGS. 5A to 5C may be similar to those described above for the aerosol provision system represented in FIGS. 1 to 4. Thus, in use, a user sucks on the mouthpiece 514, which leads to air being drawn into the interior of the aerosol provision system 500 through inlet openings in a distal end of the aerosol provision system (not shown in the figures). A controller of the aerosol provision system is configured to detect the inlet of air, for example based on a change in pressure, and activate the aerosol generator 504 in response thereto. Thus, an aerosol of the liquid formulation comprising the source liquid in the reservoir body 506 is generated in the region of the aerosol generator 504. As air is drawn through the aerosol provision system it passes the region of the aerosol generator 504 and carries some of the aerosol through the air channel 520 to the opening 516 in the mouthpiece 514.

In a manner similar to that described above, at least a portion of the inner wall of the air channel 520 is provided with a surface finish to increase the wettability of the surface of the air channel to the liquid formulation. In particular, in this example implementation, the flat surface 508 of the first component 502 and a part of the inner surface of the housing component 510 defining the air channel 520 in conjunction with the flat surface 508 are provided with a textured finish to increase the wettability of these surfaces to the liquid formulation in accordance with the principles described above (the texture is schematically represented on the flat surface 508 in FIGS. 5A and 5C). The effect of this is, as described above, a reduced likelihood of liquid formulation that has condensed onto the surface of the air channel 520 from becoming entrained in air drawn through the air channel and out through the opening 516 into a user's mouth. It will be appreciated that a surface finish to increase wettability can instead or also be applied to other interior walls of the air channel, for example those within the mouthpiece 514.

In some example implementation is the surface finish for increasing wettability may be applied relatively consistently across the surfaces. However, in accordance with some embodiments, the surface finish may be varied across the air channel wall to provide areas of different wettability for the liquid formulation. For example, a surface texture (or other surface finish) may be applied in a first area that provides a higher wettability than a surface texture (or other surface finish) applied in a second area that is adjacent to the first area so the liquid formulation can flow from between the two areas. The higher wettability of the first area means that liquid formulation that has condensed in the second area will have a tendency to be drawn to the first area. Thus, if the second area is arranged closer to an opening through which a user inhales the aerosol than the first area, this approach can help urge condensed liquid formulation to move away from the end of the aerosol provision system through which the user inhales. This can further reduce the likelihood of liquid formulation that has condensed onto the wall of the air channel from being entrained in the airflow and subsequent drawn into a user's mouth.

In some example implementations liquid formulation that has condensed onto the inner wall of the air channel may be encouraged to flow out of the air channel. For example, the aerosol provision system may be provided with what is in effect a storage (holding) surface that is in fluid communication with the air channel, but which is outside the air channel. For example, the storage surface may comprise a surface of a thin gap provided in a wall of the air channel and extending away therefrom. Thus, liquid formulation that condenses on the wall of the air channel may be drawn into the gap, and hence out of the air channel, under capillary action.

By way of an example, the interface between the reservoir body 506 and the interior of the housing 510 schematically represented in FIG. 5C which is in a region adjacent to the air channel 520 (i.e. in the vicinity of the curved surface of reservoir body 506 that is adjacent the flat surface 508) may provide this function. That is to say, liquid formulation condensing in the air channel 520 onto the flat surface 508, or onto the inner surface of the other housing 510 facing the flat surface 508, may be drawn into the gap between the curved surface of the reservoir body 506 and the housing component 510 under capillary action, as schematically represented by the series of arrows directed away from the air channel in FIG. 5C. To further enhance this effect, regions of one or other or both of the surfaces defining the gap adjacent to the air channel may be provided with a surface finish, for example surface texturing, to facilitate the flow of liquid formulation from the wall of the air channel into the interface under capillary action. For example, referring to the implementation of FIGS. 5A to 5C, regions of the outer surface 507 of the reservoir component 506 and the inner surface 511 of the housing component 510 which are outside the air channel 520 may be provided with a surface finish, e.g. surface texturing, which is the same, or similar, to that provided for regions of these surfaces defining the air channel 520. What is more, the surface finish applied in the gap adjacent to the air channel may provide for increased wettability with increasing distance from the air channel so as to facilitate the drawing of liquid formulation further into the gap, thereby leaving room for more liquid formation to be drawn into the gap.

Thus, there have been described examples of aerosol provision systems that can help ameliorate the issues discussed above with regards to mouth leakage by providing for increased wettability on an air channel surface of the aerosol provision system. In this regard, in accordance with other embodiments there are provided methods and apparatus for manufacturing such aerosol provision systems.

Figure 6:
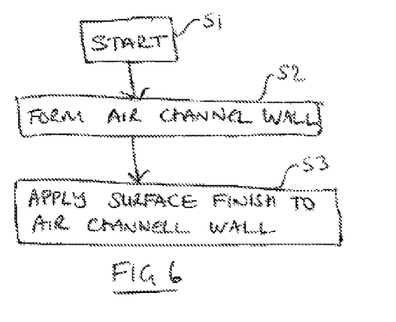

FIG. 6 schematically represents some steps of a method of manufacturing an aerosol provision system in accordance with certain embodiments. Processing starts in S1. In S2 an air channel wall component (or components) is formed. The air channel wall component(s) may be formed based generally in accordance with conventional techniques, for example molding or extrusion, having regard to the particular design of the aerosol provision system being manufactured. Thus, in respect of the example aerosol provision system represented in FIG. 5A to 5C, S2 may comprise the process of forming the reservoir body 506 part of the aerosol source component 502 and/or the housing component 510 and/or other parts of the aerosol provision system used to define the air channel to which the surface finish is applied. In S3 the relevant surface finish is applied to the wall of the air channel component(s) formed in S2. It will be appreciated that while S2 and S3 are schematically represented as separate tasks for the purposes of explanation, they may in general be performed simultaneously. For example, this may be the case if the surface finish comprises a textured surface that is introduced during molding of the relevant component(s) of the aerosol provision system that define the air channel when assembled. However, the two tasks could also be performed separately, for example if the surface finish comprises providing a service texture by abrasive roughening or applying other surface finishes such as discussed above.

Figure 7:
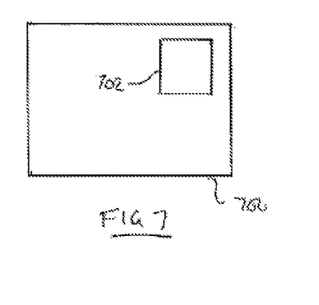

FIG. 7 schematically represents an apparatus 700 for manufacturing an aerosol provision system in accordance with certain embodiments. The apparatus 700 may be based on generally conventional techniques for manufacturing components of aerosol provision systems, but is modified to comprise a mechanism 702 for applying a surface finish to at least a portion of a component defining an air channel wall to increase wettability for the liquid formulation to be used in the aerosol provision system. In some examples the mechanism 702 may comprise a modified version of a conventional element of an apparatus for manufacturing an aerosol provision system. For example, the mechanism 702 may in effect comprise a mould for a component of an aerosol provision system which is modified to provide a surface texture as discussed above, but is otherwise conventional. In other examples, the mechanism 702 may comprise a newly-introduced component of an otherwise conventional apparatus, for example a mechanism for applying abrasive roughening or another surface finish to relevant components of the aerosol provision system (i.e. components defining the air channel to which the surface finish is applied).

Thus, there has been described an aerosol provision system, such as an electronic cigarette, that comprises an aerosol source for generating an aerosol from a source liquid comprising a liquid formulation, for example containing nicotine. The system further comprises an air channel arranged between the aerosol source and a mouthpiece opening through which a user inhales the aerosol during use. The air channel is defined by a wall, and at least a portion of an inner surface of the wall is provided with a surface finish to increase the wettability of the surface to the liquid formulation. For example, a part, or all, of the inner surface of the wall of the air channel may be provided with a textured finish. The textured finish may be provided during a molding process for the air-channel component(s) of the aerosol provision system during manufacture, for example. Increasing the wettability of the air channel can help reduce the likelihood of the aerosol condensing into droplets of the liquid formulation on the walls of the air channel and being drawn into a user's mouth therefrom.

While the above described embodiments have in some respects focused on some specific example aerosol provision systems, it will be appreciated the same principles can be applied for aerosol provision systems using other technologies. That is to say, the specific manner in which the aerosol source operates is not significant to the principles underlying certain embodiments, and configurations of aerosol source, such as disclosed in US 2011/0226236, could be used in other implementations.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An aerosol provision system comprising:
   an aerosol source for generating an aerosol from a source liquid comprising a liquid formulation; and
   an air channel wall defining an air channel for aerosol flow between the aerosol source and an opening through which a user can inhale the aerosol during use, wherein at least a portion of an inner surface of the air channel wall is provided with a surface finish to increase wettability of the air channel wall for the liquid formulation.

2. The aerosol provision system of claim 1, wherein the air channel wall comprises a substrate and the surface finish comprises a coating applied to the substrate, wherein the coating has a higher wettability for the liquid formulation than the substrate.

3. The aerosol provision system of claim 1, wherein the surface finish comprises a plasma-coating treatment.

4. The aerosol provision system of claim 1, further comprising a storage surface that is outside the air channel but in fluid communication with the air channel, wherein the storage surface is also provided with a surface finish to increase wettability of the storage surface for the liquid formulation.

5. The aerosol provision system of claim 1, wherein the aerosol source comprises a heater in contact with the source liquid, and wherein the aerosol provision system further comprises a cell or battery for supplying electrical power to the heater to heat the source liquid to generate an aerosol from the liquid formulation.

6. The aerosol provision system of claim 1, wherein the liquid formulation comprises nicotine.

7. The aerosol provision system of claim 1, wherein the surface finish comprises a surface texture.

8. The aerosol provision system of claim 7, wherein the surface texture is molded into the air channel wall.

9. The aerosol provision system of claim 7, wherein the surface texture is provided by abrasive roughening of the air channel wall.

10. The aerosol provision system of claim 1, wherein the surface finish is varied across the air channel wall to provide areas of different wettability for the liquid formulation.

11. The aerosol provision system of claim 10, wherein the areas of different wettability for the liquid formulation comprise a first area adjacent to a second area, wherein the first area is nearer to the opening through which a user can inhale the aerosol than the second area, and wherein the second area has a higher wettability for the liquid formulation than the first area.

12. The aerosol provision system of claim 1, wherein the air channel is defined by a spacing between a first component of the aerosol provision system and a second component of the aerosol provision system.

13. The aerosol provision system of claim 12, wherein at least a portion of a surface of at least one of the first or second components of the aerosol provision system at an interface between the at least one of the first or second components and adjacent to the air channel is provided with a textured surface finish to facilitate the flow of liquid formulation from the wall of the air channel into the interface under capillary action.

14. The aerosol provision system of claim 12, wherein the first component comprises a reservoir for the source liquid comprising the liquid formulation and the second component comprises a housing for the aerosol provision system.

15. The aerosol provision system of claim 12, wherein an outer surface of the first component conforms to an inner surface of the second component away from the spacing between the outer surface of the first component and the inner surface of the second component.

16. A method of manufacturing an air channel wall for an aerosol provision system comprising an aerosol source for generating an aerosol from a source liquid comprising a liquid formulation and the air channel wall defining an air channel for aerosol flow between the aerosol source and an opening through which a user can inhale the aerosol during use, wherein the method comprises:
applying a surface finish to at least a portion of the air channel wall to increase wettability of the air channel wall for the liquid formulation.

17. The method of claim 16, wherein applying a surface finish comprises applying a surface texture.

18. The method of claim 17, wherein the surface texture is applied by molding at least a portion of the air channel wall using a textured mold.

19. The method of claim 17, wherein the surface texture is applied by abrasive roughening of at least a portion of the air channel wall.

20. An apparatus for manufacturing an air channel wall for an aerosol provision system comprising an aerosol source for generating an aerosol from a source liquid comprising a liquid formulation and the air channel wall defining an air channel for aerosol flow between the aerosol source and an opening through which a user can inhale the aerosol during use, wherein the apparatus comprises:
a mechanism for applying a surface finish to at least a portion of the air channel wall to increase wettability of the air channel wall for the liquid formulation.

* * * * *